United States Patent
Cong et al.

(10) Patent No.: US 9,567,557 B2
(45) Date of Patent: Feb. 14, 2017

(54) TRAP-TYPE CARBON REPLENISHING DEVICE FOR CULTURING MICROALGAE OF OPENED POOL AND CARBON REPLENISHING METHOD THEREOF

(75) Inventors: Wei Cong, Beijing (CN); Zhongliang Sun, Beijing (CN); Ming Liu, Beijing (CN); Xia Wu, Beijing (CN); Dongmei Zhang, Beijing (CN); Shumei Wen, Beijing (CN)

(73) Assignee: Institute of Process Engineering, Chinese Academy of Sciences (CN)

( * ) Notice: Subject to any disclaimer, the term of this patent is extended or adjusted under 35 U.S.C. 154(b) by 142 days.

(21) Appl. No.: 14/396,567

(22) PCT Filed: May 7, 2012

(86) PCT No.: PCT/CN2012/075123
§ 371 (c)(1),
(2), (4) Date: Jan. 20, 2015

(87) PCT Pub. No.: WO2013/166639
PCT Pub. Date: Nov. 14, 2013

(65) Prior Publication Data
US 2015/0132830 A1    May 14, 2015

(51) Int. Cl.
*C12M 1/00* (2006.01)
*C12M 1/06* (2006.01)
*C12N 1/12* (2006.01)

(52) U.S. Cl.
CPC ............. *C12M 23/18* (2013.01); *C12M 21/02* (2013.01); *C12M 27/06* (2013.01); *C12M 27/20* (2013.01); *C12M 29/06* (2013.01); *C12N 1/12* (2013.01)

(58) Field of Classification Search
CPC ........ A01N 25/10; A01N 37/46; A01N 63/02; C08L 89/00; C09D 5/14; C09D 7/125; C09D 5/1625; C09D 5/1637; C09D 189/00; C09D 5/008; C09D 5/1668; C09D 7/1233; C09D 7/1291; C12M 21/02; C12M 23/18; C12M 27/06; C12M 27/20; C12M 29/06; B01D 3/06; B01D 53/48; B01D 53/62; B01J 19/0093; B01J 19/24; B01J 2219/00864; B01J 2219/00867;B01J 2219/00871; B01J 2/00; B01J 6/008

See application file for complete search history.

(56) References Cited

U.S. PATENT DOCUMENTS

| | | | |
|---|---|---|---|
| 8,241,634 B2 * | 8/2012 | Cong | C12M 21/02 424/195.17 |
| 9,133,044 B2 * | 9/2015 | Phattaranawik | C02F 3/301 |
| 2008/0311646 A1 * | 12/2008 | Cong | C12M 21/02 435/257.1 |
| 2012/0006744 A1 * | 1/2012 | Phattaranawik | C02F 3/301 210/605 |

FOREIGN PATENT DOCUMENTS

| | | |
|---|---|---|
| CN | 1837350 | 9/2006 |
| CN | 1982432 | 6/2007 |
| CN | 201132831 | 10/2008 |
| CN | 101724549 | 6/2010 |
| JP | H3056122 A | 3/1991 |

* cited by examiner

Primary Examiner — Debbie K Ware
(74) Attorney, Agent, or Firm — Jack Schwartz & Associates, PLLC

(57) ABSTRACT

The invention relates to the field of microalgae culture and specifically relates to a trap-type carbon supplement device and carbon supplement method for cultivating microalgae in an open pond. The trap-type carbon supplement device for cultivating microalgae in an open pond, comprises a trap-type container, a partition plate and a gas distributor, wherein the gas distributor is positioned at the culture solution inlet of the trap-type carbon supplement device; the thickness of the trap-type carbon supplement device on the side of the culture solution inlet is 0.5-2 times of the depth of the culture solution in the open pond; the gap between the lower end of the partition plate and the bottom of the trap-type container is 0.5-2 times of the thickness of the trap-type carbon supplement device on the side of the culture solution inlet; the upper end of the partition plate is higher than the wall of the trap-type container; and the width of the partition plate is matched with the trap-type container. The carbon supplement device of the invention can make the gas-liquid contact time longer and reduce the depth of the trap-type container, therefore it can reduce the flow resistance of the liquid in the carbon supplement device and save energy consumption.

11 Claims, 3 Drawing Sheets

TRAP-TYPE CARBON REPLENISHING DEVICE FOR CULTURING MICROALGAE OF OPENED POOL AND CARBON REPLENISHING METHOD THEREOF

FIELD OF THE INVENTION

The invention relates to the field of mass cultivation of microalgae and specifically relates to a trap-type carbon supplement device and carbon supplement method for cultivating microalgae in an open pond.

BACKGROUND OF THE INVENTION

Microalgae can produce a variety of chemical products by fixing carbon dioxide through photosynthesis. Some microalgae can produce aliphatic hydrocarbons, for example, the hydrocarbon production of *botryococcus* can reach 15%-75% of dry cell weight; some microalgae can accumulate glycogen; some microalgae can accumulate glycerol, wherein the lipid content of many microalgae can reach 60% or above of the dry cell weight. The average combustion heat of fuel oil obtained by pyrolysis of algae biomass can be up to 33 MJ/kg. Microalgae can be cultured in seawater, salty water or semi-salty water, avoiding scrambling for land and freshwater resources with crops, and can be cultured with waste water. So, microalgae could be an important source to obtain biological resources in regions lack of freshwater or with barren land. Therefore microalgae are expected to be important sources for future energy and chemical products.

The carbon in microalgae cells accounts for more than a half of the dry cell weight of the cells, and the algae cells can fix carbon dioxide as their own components through photosynthesis in growing process, so that the supply of carbon sources should be assured in the culture medium in the algae culture process. The inorganic carbon sources in the algae culture medium exist in three forms, namely $HCO_3^-$, $CO_3^{2-}$ and free $CO_2$. The ratio of the three forms of carbon sources in water varies with the pH value of the culture medium. If $NaHCO_3$ is used as the carbon source, with the dissociation of $HCO_3^-$ and the utilization of $CO_2$, the pH value of the culture medium rises continually, more than half of the added $NaHCO_3$ is converted to $Na_2CO_3$ which could not be utilized by algae, resulting a waste and considerable consumption of carbon source; moreover, the medium is difficult to be recycled because of the rise of its pH value. If $CO_2$ is used as the carbon source, which is directly utilized by the microalgae, then the problem that the pH value of the culture medium rises can be avoided, which is beneficial for maintaining an desirable culture environment and allows the medium to be used repeatedly or for an extended period.

Cultivation in an open pond is a traditional and simple mode of microalgae culture, and is also recognized as a mature microalgae culture technology currently. It has the advantages of having a simple construction and being easy to operate, and has been applied to commercial production of *spirulina, chlorella* and *Dunaliella salina* (Chaumont D., J. Appl. Phycol., 1993, 5:593-604; Richmond A., Progress in Physiological Research, Vol.7, Biopress, Bristol., 1990, 269-330; Borowitzka L. T., Bioresource Technology, 1991, 38: 251-252). However, the depth of the culture solution in a traditional open pond is usually kept at 20-30 cm, if the $CO_2$ is directly aerated into the open pond in a bubbling way, due to the very short residence time of the bubbles in the culture solution, the absorption efficiency of the $CO_2$ is very low-only 13%-20% of the $CO_2$ is absorbed (Becker E W, Microalgae: biotechnology and microbiology, Cambridge University Press, Cambridge, 1994, pp 293).

Ferreira et al. (Ferreira B S, Fernandes H L, Reis A and Mateus M. Microporous hollow fibers for carbon dioxide absorption: mass transfer model fitting and the supplying of carbon dioxide to microalgae cultures. Journal of Chemical Technology and Biotechnology, 1998, 71: 61-70) utilized a hollow fiber membrane to enhance gas-liquid mass transfer, so as to improve the absorption efficiency of the $CO_2$, but the method is high in cost, and the hollow fiber membrane is prone to be fouled.

As for the method of L I Yeguang, H U Hongjun, ZHANG Liangjun and CHEN Zhixiang (Study on $CO_2$ supply technique for *spirulina* production, Journal of Wuhan Botanical Research, 1996, 14 (4): 349-356), a gas-cover in size of several square meters is arranged on the surface of microalgae culture solution, and carbon dioxide gas is introduced into the gas-cover, so that the carbon dioxide is transferred into the culture solution through the water surface shrouded by the cover. The problems with this method are as follows: the specific interfacial area for gas-liquid exchange is small; the mass transfer rate is lowered down due to accumulation of oxygen and nitrogen in the gas-cover, and the oxygen and nitrogen need to be ventilated frequently, so part of the carbon dioxide in the gas-cover is wasted; for a gas source containing low-content carbon dioxide, the absorption efficiency of the carbon dioxide is very low; when the pressure in the gas-cover is slightly higher, the gas may leak out from the edge of the gas-cover through the liquid surface outside the gas-cover. Groove type carbon supplement method (CN200610018771.9, Device for Supplementing Carbon Dioxide into Microalgae Cultivation Pond) is as follows: a deep groove is dug and located beside a culture pond to enable the culture solution to flow through the deep groove, a gas sparger is arranged at the bottom of the groove, through which the carbon dioxide is supplied into the culture solution. The method may disrupt the spatial layout of the traditional open pond; and furthermore, the culture solution in the groove is not mixed well, the bottom of the groove becomes a dead zone for mass transfer after being saturated with carbon dioxide after a period of sparging, and then the deep groove does not function as a mass exchanger.

CONG Wei et al. (CN200510126465.2, Carbon Supply Device for Large-scale Culture of Microalgae and its Application and Use) develop a trap type carbon supplement device comprising a trap-type container; a partition plate and a gas distributor as shown in FIG. 1 for directly supplementing $CO_2$ into the culture solution in an open pond, wherein the culture solution can form a circulation in the trap type carbon supplement device, thereby the time for gas-liquid contact is greatly prolonged; moreover, gas is supplied from the bottom of the trap type carbon supplement device; so that the absorption efficiency of $CO_2$ is greatly improved. However, the carbon supplement device increases the flow resistance in the open pond, thereby resulting in increased electrical energy consumption for driving the fluid with a paddle wheel under the same flow velocity, and relatively more construction workload. According to the carbon supplement device disclosed in Patent Application No. CN200510126465.2, a gas distributor is positioned at the bottom of the trap-type carbon supplement device, as shown in FIG. 1, no matter whether the partition plate is mounted on the left side(upstream side), in the middle or on the right side(downstream side) in the trap-type container, only a part of the volume of the carbon supplement device (the upstream side or the downstream side of the partition plate) functions as a gas-liquid exchanger, so the utilization of the volume of the carbon supplement device is not high. If the regions on both sides of the partition plate in the carbon supplement device can become gas-liquid exchange regions, then the depth of the trap-type container of the carbon supplement device can be reduced to about one half of its present depth without loss of absorption efficiency of carbon dioxide, so that the flow resistance of the fluid in the trap-type carbon supplement device is reduced and thus energy consumption is saved.

SUMMARY OF THE INVENTION

An objective of the invention is to provide a trap-type carbon supplement device for cultivating microalgae in an open pond, to solve the above problems.

Another objective of the invention is to provide a carbon supplement method for cultivating microalgae in an open pond.

The solution of the present invention is to move the gas distributor of the carbon supplement device of patent CN200510126465.2 from the bottom of the trap-type carbon supplement device to the culture solution inlet of the trap-type carbon supplement device, so that when the culture solution flows into the trap-type carbon supplement device from the culture solution inlet of the trap-type carbon supplement device under the driving of a stirrer (an paddle wheel is conventionally used in the art), by maintaining the appropriate flow velocity at the culture solution inlet, bubbles containing carbon dioxide released from the gas distributor do not move upwards but go down together with the culture solution, meanwhile, gas-liquid exchange occurs (the region is called as downcomer of the trap-type carbon supplement device); and then both the bubbles and the culture solution pass through the gap between the lower end of the partition plate and the bottom of the trap-type container, to enter the region on the other side of the partition plate (the region is called as riser of the trap-type carbon supplement device) and further flow out of the trap-type carbon supplement device. With such an arrangement, the regions on both sides of the partition plate function as gas-liquid exchange regions, so the residence time for the culture solution to flow through both the downcomer and the riser of the trap-type carbon supplement device becomes gas-liquid contact time, thereby the gas-liquid contact time is prolonged in comparison with the carbon supplement device of patent CN200510126465.2, and the depth of the trap-type container of the existing carbon supplement device can be reduced.

The present trap-type carbon supplement device for cultivating microalgae in an open pond comprises a trap-type container 1, a partition plate 2 and a gas distributor 3, wherein the gas distributor 3 is positioned at the culture solution inlet of the trap-type carbon supplement device 6; the thickness of the trap-type carbon supplement device 6 on the side of the culture solution inlet (the downcomer, confined by the partition plate 2 and the wall of the trap-type container 1) is 0.5-2 times of the depth of the culture solution in the open pond; the gap between the lower end of the partition plate 2 and the bottom of the trap-type container 1 is 0.5-2 times of the thickness of the trap-type carbon supplement device 6 on the side of the culture solution inlet; and the upper end of the partition plate 2 is higher than the wall of the trap-type container 1, and the width of the partition plate 2 is matched with the trap-type container 1.

According to the trap-type carbon supplement device of the invention, the thickness of the trap-type carbon supplement device 6 on the side of the culture solution inlet is 5-50 cm. Under the normal depth and flow velocity of culture solution in an open pond, the thickness of the trap-type carbon supplement device 6 on the side of the culture solution inlet can ensure the liquid in the downcomer to flow at a velocity to drag the bubbles, so that most of the bubbles go down together with the culture solution.

According to the trap-type carbon supplement device of the invention, preferably, the trap-type container 1 has a depth of 15-150 cm, a thickness of 20-200 cm and a width equal to that of the open pond.

According to the trap-type carbon supplement device of the invention, the trap-type container 1 has a flat bottom, a flat bottom with round corners, a conical bottom or a semi-circular bottom, and can be made of cement, a plastic plate, a stainless steel plate, bricks, the same material as the bottom of the open pond or the like.

According to the trap-type carbon supplement device of the invention, the partition plate 2 has a thickness of 1-5 cm and is made of a plastic plate, a stainless steel plate, a wood plate and the like, which can be machinable and has a certain strength.

According to the trap-type carbon supplement device of the invention, the gas spreading surface (plate) of the gas distributor 2 is made of porous material. The gas distributor 2 can be a pipe-like gas distributor or a gas distributor composed of several gas sparging heads connected to a gas delivering pipe. The gas distributor can be hard, such as a porous ceramic pipe or a glass sand core, or be soft, such as a commercially available aeration hose or a variable-pore aeration hose.

According to the trap-type carbon supplement device of the invention, when the depth of the culture solution in the open pond is relatively small, the stirrer of the open pond can be lowered to a position where the blade tip of the stirrer is lower than the bottom of the open pond. The present trap-type carbon supplement device can be constructed together with the stirrer of the open pond, that is to say, the blade tip/tips of the stirrer/stirrers 5 arranged on one side or two sides of the carbon supplement device is/are lower than the bottom of the open pond, or the blade tip/tips of the stirrer/stirrers 5 arranged on one side or two sides of the partition plate 2 is/are lower than the bottom of the open pond. The stirrer 5 is located above a semi-circular arc-shaped groove or a ¼ circular arc-shaped groove, wherein the ¼ circular arc-shaped groove can be linked up with the side wall of the trap-type container 1, and the bottom of the circular arc-shaped groove is higher than the bottom of the trap-type container 1 or directly linked up with the bottom of the trap-type container 1.

According to the carbon supplement method for cultivating microalgae in an open pond based on the trap-type carbon supplement device of the invention, the trap-type carbon supplement device is embedded into the bottom of the open pond, wherein the upper edge of the trap-type container of the trap-type carbon supplement device is aligned with the bottom of the open pond; the partition plate is above the liquid surface of the culture solution in the open pond; the porous gas distributor is positioned at the culture solution inlet of the trap-type carbon supplement device, so that the culture solution can flow into the downcomer of the trap-type carbon supplement device from the culture solution inlet of the trap-type carbon supplement device under the driving of the stirrer (a paddle wheel is conventionally used as the stirrer in the art), to be in contact with the $CO_2$ bubbles released from the gas distributor. The culture solution mixed with the $CO_2$ bubbles pass through the gap at the bottom of the carbon supplement device, and then flows through the riser and finally flows out of the culture solution outlet of the trap-type carbon supplement device. With such an arrangement, the gas-liquid contact time is greatly prolonged. On the other hand, carbon dioxide gas (or gas mixture containing carbon dioxide) becomes into very small bubbles after passing through the gas distributor, so that the gas-liquid interfacial area is drastically increased, which leads to the absorption efficiency of the carbon dioxide greatly improved;

the flow velocity of the culture solution on the side of the culture solution inlet of the trap-type carbon supplement device is 15-100 cm/s;

the flow rate of the $CO_2$ of the gas distributor in the trap-type carbon supplement device, calculated as pure $CO_2$ under standard condition, is 0.1-20 L/min per meter of the width of the open pond.

According to the carbon supplement method of the invention, preferably, the depth of the culture solution in the open pond is 2-30 cm.

According to the carbon supplement method of the invention, wherein the $CO_2$ is one or more of cleaned flue gas, industrial $CO_2$ gas, pure $CO_2$ gas or air mixed with $CO_2$, or liquid $CO_2$.

The medium for cultivating microalgae can be any known medium which is suitable for microalgae growth in the art, such as Zarrouk medium, SM medium, $ASP_2$ medium, BG-11 medium and the like, and can also be a medium which is specially needed for a certain alga or a medium which needs $CO_2$ in the culture process.

The carbon supplement device and carbon supplement method of the present invention can be used for supplementing $CO_2$ in large-scale culture process of various microalgae in an open pond, including *spirulina, scenedesmus, haematococcus pluvialis, Dunaliella salina, chlorella, chlamydomonas* and other various microalgae.

According to the invention, microalgae cells can be cultivated in the open pond by effectively utilizing carbon dioxide for carbon source, which greatly reduces production cost. Compared with the carbon supplement device of patent CN200510126465.2, the carbon supplement device of the invention can make the gas-liquid contact time longer and reduce the depth of the trap-type container, so it can reduce the flow resistance of the liquid in the carbon supplement device and save energy consumption.

Figure 1:
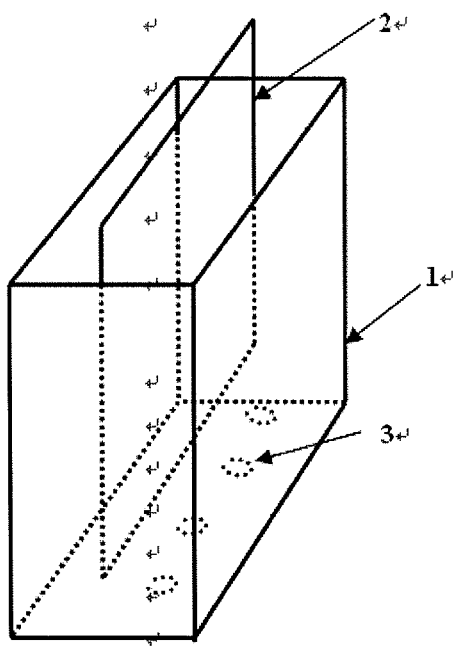
FIG. 1 is a schematic diagram of a trap-type carbon supplement device of Patent Application No. CN200510126465.2.

DESCRIPTION OF THE REFERENCE NUMERALS 1. trap-type container; 2. partition plate; 3. gas distributor 4. execution mechanism; 5. Stirrer; 6. trap-type carbon supplement device; 7. liquid surface of microalgae culture solution; 8. flowmeter; 9. pressure gauge; 10. pH sensor 11. control device; 12. $CO_2$ gas source

DETAILED DESCRIPTION OF THE INVENTION

Embodiment 1

Figure 2:
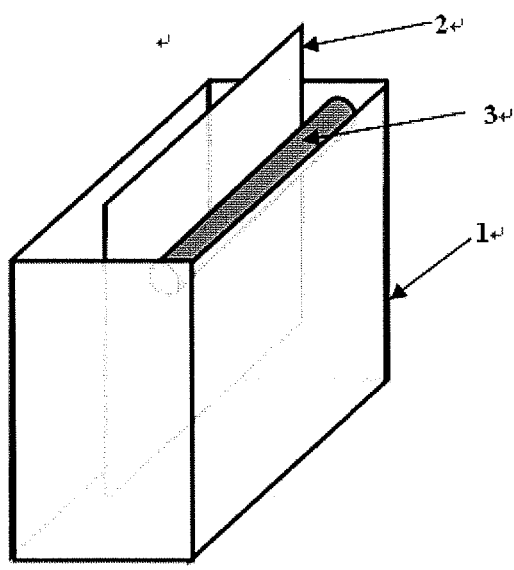
FIG. 2 is a schematic diagram of a trap-type carbon supplement device of the invention.
Figure 3:
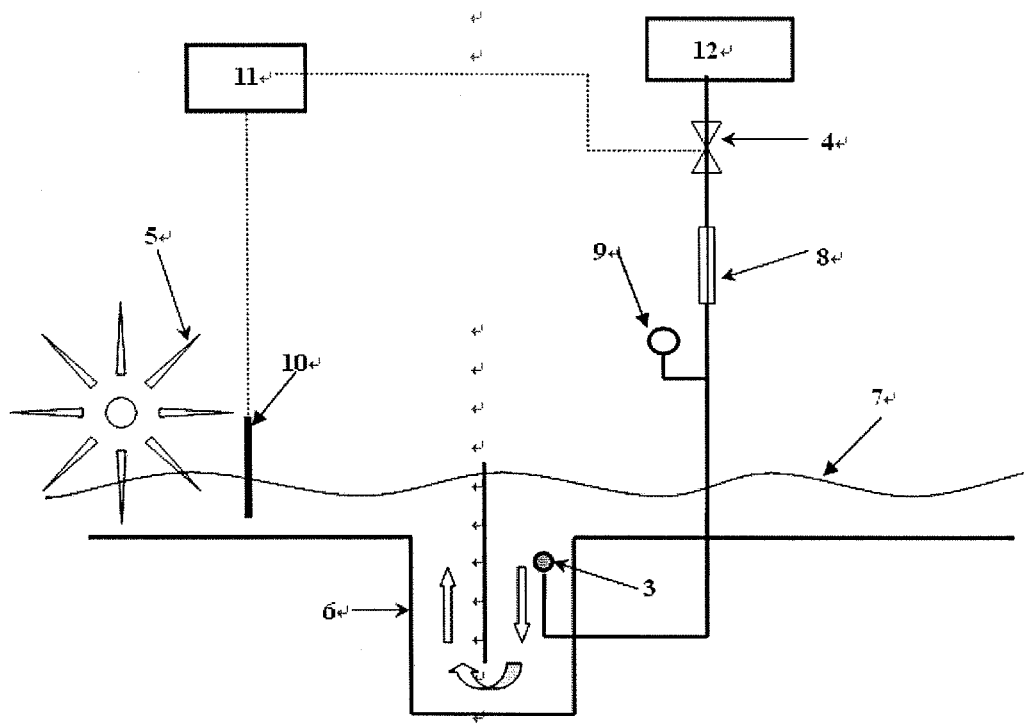
FIG. 3 is a schematic diagram of a system utilizing the trap-type carbon supplement device of the invention for automatic carbon supplement.

*Spirulina* is cultured in a raceway-type culture pond (a most common open pond, referred as raceway pond). The flow channel of the raceway pond has a perimeter of 70 m and a width of 3 m. A stirrer 5 comprises four groups of steel paddle wheels driven by a rotating shaft, with each paddle wheel comprising four blades spaced by 90-degree, the blades of two adjacent paddle wheels staggered by 45-degree, the rotating shaft being driven by an alternating current motor through variable gearing, and the radius of the stirrer 5 in rotating being 50 cm. The sectional views of the stirrer 5 and a trap-type carbon supplement device 6 are shown in FIG. 3. FIG. 2 shows a carbon supplement device 6, which comprises a trap-type container 1, a partition plate 2 and a gas distributor 3, wherein the gas distributor 3 is positioned at the culture solution inlet of the trap-type carbon supplement device 6. The trap-type container 1 having a depth of 50 cm, a width of 3 m (which is consistent with width of the raceway pond) and a thickness of 62 cm, with the bottom of the trap-type container 1 being a flat bottom with round corners. The trap-type container 1 is made of cement (which is the same with the material of the raceway pond, and the trap-type container is dug out at the bottom of the raceway pond). The partition plate 2 is a wood plate with a thickness of 2 cm and its width is matched with that of the trap-type container 1. The gap between the lower end of the partition plate 2 and the bottom of the trap-type container 1 is 20 cm, and the thickness of the trap-type carbon supplement device 6 on the side of the culture solution inlet (namely the thickness of the downcomer of the trap-type carbon supplement device) is 20 cm. The gas distributor 3, a variable-pore aeration hose with a length of 2.8 m and a diameter of 65 mm, is positioned at the central position of the culture solution inlet of the trap-type carbon supplement device 6, wherein the vertical position of the upper edge of the gas distributor 3 is aligned with the bottom of the raceway pond. The culture solution is driven by the stirrer 5 to flow along the flow channel of the raceway pond for a circle, enters the culture solution inlet of the trap-type carbon supplement device 6 to be in contact with the $CO_2$ bubbles released from the gas distributor 3, and then goes down together with the $CO_2$ bubbles to pass through the gap between the lower end of the partition plate 2 and the bottom of the trap-type container 1, goes up to flow out of the culture solution outlet of the trap-type carbon supplement device 6, and finally returns to the stirrer 5 for further circulations.

The carbon supplement procedure is controlled in an automatic mode, such as the method disclosed in application with No. CN200410009360.4, and a system for implementing the control is shown in FIG. 3, wherein, a pH sensor 10 is a commercially available pH sensor which is immersed below the liquid surface of the microalgae culture solution 7, a control device 11 is a pH meter with a switch controller, a $CO_2$ gas source 12 is pure carbon dioxide gas from a steel cylinder, and an execution mechanism 4 is a two-position normally-closed solenoid valve (the flow diameter of the valve is 8 mm). The carbon dioxide delivering valve (the execution mechanism 4) is controlled to be open or closed according to the pH value of the culture solution.

The algae species is *Spirulina Platensis*, which comes from the Freshwater Algae Culture Collection of the Institute of Hydrobiology, Chinese Academy of Sciences, and is numbered as No. 439. The medium is Zarrouk medium, wherein the initial concentration of sodium bicarbonate is 0.05 mol/L. The average depth of the culture solution in the raceway pond is 20 cm, and the inoculation density of algae cells is 0.3 g (dry cell weight)/L. The range of the pH value of the culture solution is controlled within 9.5-9.6. When the pH value of the culture solution rises to 9.5, automatic carbon supplement procedure is initiated, during this procedure the flow rate of the carbon dioxide gas of the gas distributor 3 of the trap-type carbon supplement device 6 (while the execution mechanism 4 is open) is 6L/min (pure carbon dioxide, standard conditions). By adjusting the rotational speed of the motor, the flow velocity of the culture solution in the raceway pond is enabled to be about 25 cm/s, which makes the flow velocity of the liquid in the downcomer and the riser of the trap-type carbon supplement device 6 to be about 25 cm/s and 12.5 cm/s respectively.

The concentration of other nutrient salts is detected and supplemented timely if necessary every day, and a small amount of water is also supplemented to make up for the loss of water caused by evaporation. After the culture procedure is continuously carried on for 6 days, the density of the algae cells reaches 0.70 g (dry cell weight)/L, and the production of the algae cells per unit area reaches 13.3 g (dry cell weight)/$m^2$.d. The composition and the content of conventional components, amino acids, fatty acids and carotenoids of the obtained spirulina algae powder are basically consistent with those reported in prior art documents. From calculation according to material balance the utilization efficiency of the carbon dioxide from the steel cylinder reaches 88%. The electrical energy consumption for stirring is 1.10 W/$m^2$.

While, in the same raceway pond with the same trap-type carbon supplement device as that mentioned above except that the gas distributor is positioned at the bottom of the trap-type carbon supplement device as the way disclosed in patent CN200510126465.2, under the same culture conditions, the production of the algae cells per unit area is 13.1 g(dry cell weight)/$m^2$.d in the culture procedure for 7 days, and the utilization efficiency of the carbon dioxide from the steel cylinder is 77%.

While, in the same raceway pond as that mentioned above except that the depth of the trap-type container of the trap-type carbon supplement device is 1.2 m and the gas distributor is positioned at the bottom of the trap-type carbon supplement device as the way disclosed in patent CN200510126465.2, under the same culture conditions, the production of the algae cells per unit area is 13.2 g (dry cell weight)/$m^2$.d in the culture procedure for 7 days, the utilization efficiency of the carbon dioxide from the steel cylinder is 87%, and the electrical energy consumption for the stirring is 1.33 W/$m^2$.

Embodiment 2

The features that are the same as those of embodiment 1 are omitted. In this embodiment, the trap-type container has a depth of 150 cm and a thickness of 62 cm; the gap between the lower end of the partition plate and the bottom of the trap-type container is 30 cm; the thickness of the downcomer of the trap-type carbon supplement device is 15 cm. The average depth of the culture solution in the raceway pond is 30 cm. The inoculation density of the algae cells is 0.2 g (dry cell weight)/L. The range of the pH value of the culture solution is controlled within 9.7-9.8. The flow velocity of the culture solution in the raceway pond is about 20 cm/s, and the flow velocity of the liquid in the downcomer and the riser of the trap-type carbon supplement device is about 40 cm is and 13.3 cm/s respectively. After the culture procedure is continuously carried on for 6 days, the utilization efficiency of the carbon dioxide from the steel cylinder is 90%. The electrical energy consumption for the stirring is 1.15 W/$m^2$.

Embodiment 3

The features that are the same as those of embodiment 1 are omitted. In this embodiment, the trap-type container has a depth of 70 cm and a thickness of 202 cm; the gap between the lower end of the partition plate and the bottom of the trap-type container is 50 cm; the thickness of the downcomer of the trap-type carbon supplement device is 50 cm. The average depth of the culture solution in the raceway pond is 25 cm. The inoculation density of the algae cells is 0.25 g (dry cell weight)/L. The range of the pH value of the culture solution is controlled within 9.9-10.0. The flow velocity of the culture solution in the raceway pond is about 50 cm/s, and then the flow velocity of the liquid in the downcomer and the riser of the trap-type carbon supplement device is about 25 cm/s and 8.3 cm/s respectively. After the culture procedure is continuously carried on for 6 days, the utilization efficiency of the carbon dioxide from the steel cylinder is 93%. The electrical energy consumption for the stirring is 1.19 W/$m^2$.

Embodiment 4

The features that are the same as those of embodiment 1 are omitted. In this embodiment, the trap-type container has a depth of 20 cm and a thickness of 62 cm; the gap between the lower end of the partition plate and the bottom of the trap-type container is 15 cm; the thickness of the downcomer of the trap-type carbon supplement device is 30 cm. The average depth of the culture solution in the raceway pond is 15 cm. The inoculation density of the algae cells is 0.4 g (dry cell weight)/L. The range of the pH value of the culture solution is controlled within 9.8-9.9. The flow velocity of the culture solution in the raceway pond is about 40 cm/s, and then the flow velocity of the liquid in the downcomer and the riser of the trap-type carbon supplement device is about 20 cm/s and 20 cm/s respectively. After the culture procedure is continuously carried on for 6 days, the utilization efficiency of the carbon dioxide from the steel cylinder is 76%. The electrical energy consumption for the stirring is 1.04 W/$m^2$.

Embodiment 5

The features that are the same as those of embodiment 1 are omitted. In this embodiment, the trap-type container has a depth of 70 cm and a thickness of 22 cm; the gap between the lower end of the partition plate and the bottom of the trap-type container is 10 cm; the thickness of the downcomer of the trap-type carbon supplement device is 10 cm.

The gas introduced into the trap-type container is air containing 15% of carbon dioxide (simulated flue gas), wherein the flow rate of the carbon dioxide (while the execution mechanism 4 is open) is 6L/min (pure carbon dioxide, standard conditions). The average depth of the culture solution in the raceway pond is 10 cm. The inoculation density of the algae cells is 0.6 g (dry cell weight)/L. The range of the pH value of the culture solution is controlled within 9.6-9.7. The flow velocity of the culture solution in the raceway pond is about 15 cm/s, and then the flow velocity of the liquid in the downcomer and the riser of the trap-type carbon supplement device is about 15 cm/s and 15 cm/s respectively. After the culture procedure is continuously carried on for 6 days, the utilization efficiency of the carbon dioxide from the steel cylinder is 84%. The electrical energy consumption for the stirring is 0.96 W/m$^2$.

Embodiment 6

Figure 4:
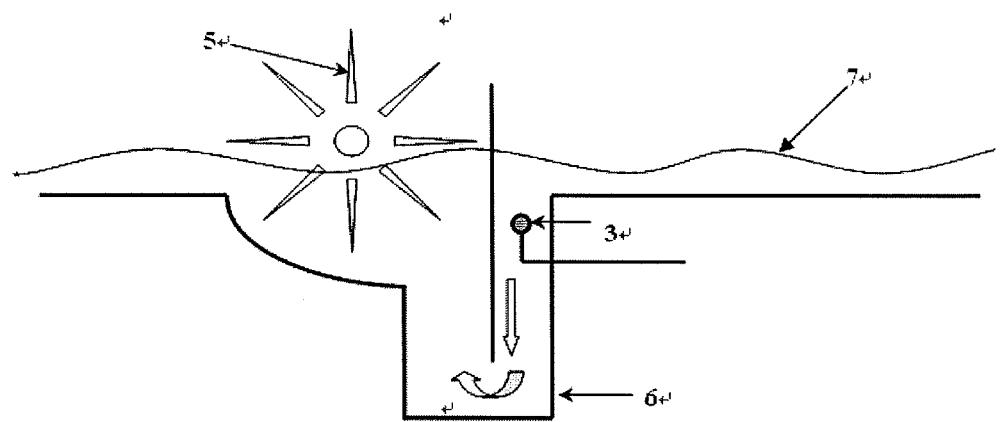
FIG. 4 is a schematic diagram of the trap-type carbon supplement device of the invention, in which a stirrer whose blade tip is lower than the bottom of the open pond is arranged on one side of the partition plate (a ¼ circular arc-shaped groove is linked up with the side wall of the trap-type container, and the bottom of the circular arc-shaped groove is higher than the bottom of the trap-type container).

The features that are the same as those of embodiment 1 are omitted. In this embodiment, the structure of the trap-type carbon supplement device is shown in FIG. 4, to be specific, a ¼ circular arc-shaped groove with a radius of 52 cm and a depth of 10 cm is dug out beside the trap-type carbon supplement device, wherein the bottom of the ¼ circular arc-shaped groove is linked up with the side wall of the trap-type container such that the blade tip of the stirrer is lower than the bottom of the raceway pond by 8 cm. Furthermore, the trap-type container has a depth of 70 cm and a thickness of 22 cm; the gap between the lower end of the partition plate and the bottom of the trap-type container is 10 cm; the thickness of the downcomer of the trap-type carbon supplement device is 5 cm. The average depth of the culture solution in the raceway pond is 5 cm. The inoculation density of the algae cells is 1.0 g (dry cell weight)/L. The range of the pH value of the culture solution is controlled within 10.1-10.2. The flow velocity of the culture solution in the raceway pond is about 15 cm/s, and then the flow velocity of the liquid in the downcomer and the riser of the trap-type carbon supplement device is about 15 cm/s and 5 cm/s respectively. After the culture procedure is continuously carried on for 6 days, the utilization efficiency of the carbon dioxide from the steel cylinder is 85%. The electrical energy consumption for the stirring is 1.04 W/m$^2$.

Embodiment 7

The features that are the same as those of embodiment 1 are omitted. The depth of the trap-type container is 70 cm and the thickness is 62 cm; the gap between the lower end of the partition plate and the bottom of the trap-type container is 20 cm; and the thickness of the downcomer of the trap-type carbon supplement device is 20 cm. *Chlorella* sp. is cultivated in the open pond, and the medium is BG-11 medium with NaNO$_3$ as nitrogen source. The average depth of the culture solution in the raceway pond is 20 cm. The inoculation density of the algae cells is 0.3 g (dry cell weight)/L. The range of the pH value of the culture solution is controlled within 7.5-7.6. The flow velocity of the culture solution in the raceway pond is about 20 cm/s, and then the flow velocity of the liquid in the downcomer and the riser of the trap-type carbon supplement device is about 20 cm/s and 10 cm/s respectively. After the culture procedure is continuously carried on for 6 days, the utilization efficiency of the carbon dioxide from the steel cylinder is 84%. The electrical energy consumption for the stirring is 1.08 W/m$^2$.

Embodiment 8

Figure 6:
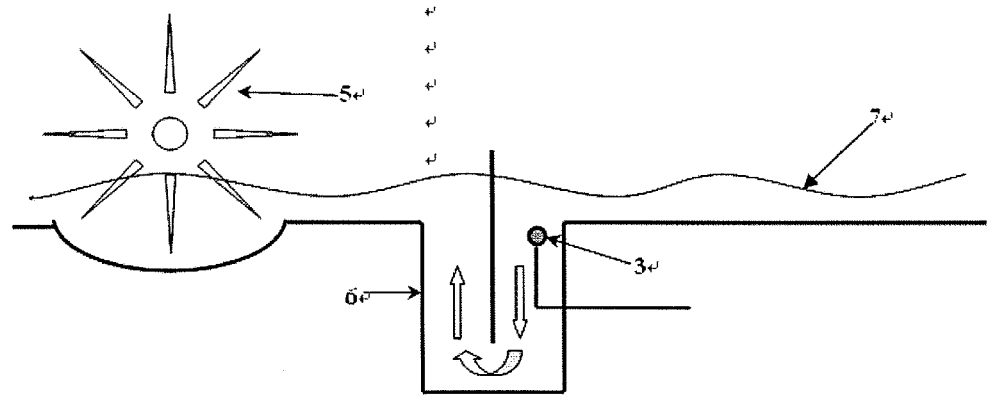
FIG. 6 is a schematic diagram of the trap-type carbon supplement device of the invention, in which a stirrer whose blade tip is lower than the bottom of the open pond is arranged on one side of the trap-type carbon supplement device(a semi-circular arc-shaped groove).

The features that are the same as those of embodiment 1 are omitted. In this embodiment, the structure of the trap-type carbon supplement device is shown in FIG. 6, to be specific, a semi-circular arc-shaped groove with a radius of 52 cm and a depth of 10 cm is dug out 10 m away from the trap-type carbon supplement device such that the blade tip of the stirrer is lower than the bottom of the raceway pond by 8 cm. Furthermore, the trap-type container has a depth of 70 cm and a thickness of 22 cm; the gap between the lower end of the partition plate and the bottom of the trap-type container is 10 cm; the thickness of the downcomer of the trap-type carbon supplement device is 5 cm. *Scenedesmus* sp. is cultivated in the open pond, and the medium is BG-11 medium with NaNO$_3$ as nitrogen source. The average depth of the culture solution in the raceway pond is 5 cm. The inoculation density of the algae cells is 1.0 g (dry cell weight)/L. The range of the pH value of the culture solution is controlled within 7.4-7.5. The flow velocity of the culture solution in the raceway pond is about 15 cm/s, and then the flow velocity of the liquid in the downcomer and the riser of the trap-type carbon supplement device is about 15 cm/s and 5 cm/s respectively. After the culture procedure is continuously carried on for 6 days, the utilization efficiency of the carbon dioxide from the steel cylinder is 81%. The electrical energy consumption for the stirring is 1.05 W/m$^2$.

Embodiment 9

Figure 5:
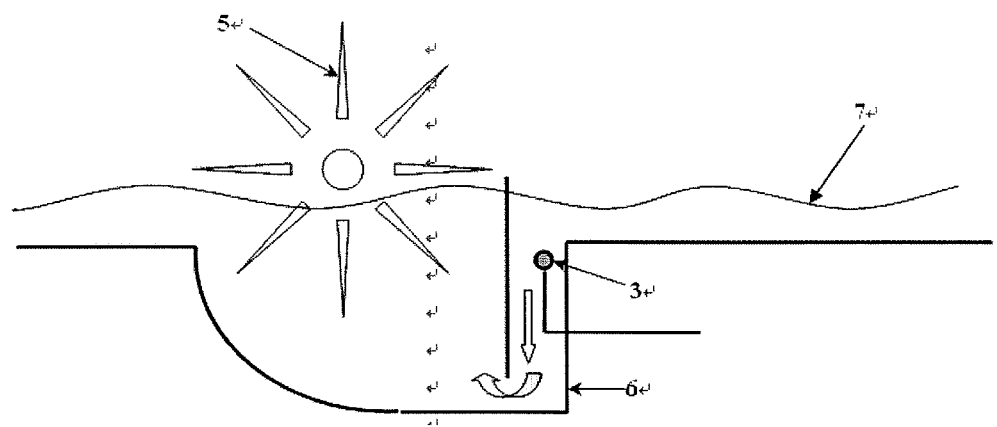
FIG. 5 is a schematic diagram of the trap-type carbon supplement device of the invention, in which a stirrer whose blade tip is lower than the bottom of the open pond is arranged on one side of the partition plate (a ¼ circular arc-shaped groove is linked up with the bottom of the trap-type container).

The features that are the same as those of embodiment 1 are omitted. In this embodiment, the structure of the trap-type carbon supplement device is shown in FIG. 5, to be specific, a ¼ circular arc-shaped groove with a radius of 35 cm and a depth of 35 cm is dug out beside the trap-type carbon supplement device, wherein the bottom of the ¼ circular arc-shaped groove is linked up with the bottom of the trap-type container such that the blade tip of the stirrer is lower than the bottom of the raceway pond by 20 cm. Furthermore, the trap-type container has a depth of 35 cm and the thickness of the flat bottom region without the groove is 27 cm; the gap between the lower end of the partition plate and the bottom of the trap-type container is 10 cm; the thickness of the downcomer of the trap-type carbon supplement device is 5 cm. The average depth of the culture solution in the raceway pond is 5 cm. The inoculation density of the algae cells is 1.0 g (dry cell weight)/L. The range of the pH value of the culture solution is controlled within 10.1-10.2. The flow velocity of the culture solution in the raceway pond is about 20 cm/s, and then the flow velocity of the liquid in the downcomer and the riser of the trap-type carbon supplement device is about 20 cm/s and 1.82 cm/s respectively. After the culture procedure is continuously carried on for 6 days, the utilization efficiency of the carbon dioxide from the steel cylinder is 80%. The electrical energy consumption for the stirring is 1.06 W/m$^2$.

The invention claimed is:

1. A trap-type carbon supplement device for cultivating microalgae in an open pond, comprises a trap-type container, a partition plate and a gas distributor, wherein the gas distributor is positioned at the culture solution inlet of the trap-type carbon supplement device; the thickness of the trap-type carbon supplement device on the side of the culture solution inlet is 0.5-2 times of the depth of the culture solution in the open pond; the gap between the lower end of the partition plate and the bottom of the trap-type container is 0.5-2 times of the thickness of the trap-type carbon supplement device on the side of the culture solution inlet; the upper end of the partition plate is higher than the wall of the trap-type container; and the width of the partition plate is matched with the trap-type container.

2. The trap-type carbon supplement device according to claim 1, wherein the thickness of the trap-type carbon supplement device on the side of the culture solution inlet is 5-50 cm.

3. The trap-type carbon supplement device according to claim 1, wherein the depth of the trap-type container is 15-150 cm, the thickness thereof is 20-200 cm, and the width thereof is consistent with that of the open pond.

4. The trap-type carbon supplement method according to claim 1, wherein the trap-type container has a flat bottom, a flat bottom with round corners, a conical bottom or a semi-circular bottom.

5. The trap-type carbon supplement device according to claim 1, wherein the thickness of the partition plate is 1-5 cm.

6. The trap-type carbon supplement device according to claim 1, wherein the blade tip/tips of a stirrer/stirrers arranged on one side or two sides of the carbon supplement device is/are lower than the bottom of the open pond, or the blade tip/tips of a stirrer/stirrers arranged on one side or two sides of the partition plate is/are lower than the bottom of the open pond.

7. A carbon supplement method for cultivating microalgae in an open pond based on the trap-type carbon supplement device of claim 1, wherein the trap-type carbon supplement device is embedded into the bottom of the open pond, the upper edge of the trap-type container of the trap-type carbon supplement device is aligned with the bottom of the open pond; the partition plate is above the liquid surface of the culture solution in the open pond, so that the culture solution can flow into the downcomer of the trap-type carbon supplement device from the culture solution inlet of the trap-type carbon supplement device under the driving of the stirrer(s), to be in contact with the $CO_2$ bubbles released from the gas distributor; then the culture solution mixed with the $CO_2$ bubbles flows through the riser and finally flows out of the culture solution outlet of the trap-type carbon supplement device;
   the flow velocity of the culture solution on the side of the culture solution inlet of the trap-type carbon supplement device is 15-100 cm/s; and
   the flow rate of the $CO_2$ of the gas distributor in the trap-type carbon supplement device, calculated as pure $CO_2$ under standard condition, is 0.1-20 L/min per meter of the width of the open pond.

8. The carbon supplement method according to claim 7, wherein the depth of the culture solution in the open pond is 2-30 cm.

9. The carbon supplement method according to claim 7, wherein the $CO_2$ is one or more of cleaned flue gas, industrial $CO_2$ gas, pure $CO_2$ gas or air mixed with $CO_2$, or liquid $CO_2$.

10. The carbon supplement method according to claim 7, wherein the medium for cultivating microalgae is Zarrouk medium, SM medium, $ASP_2$ medium or BG-11 medium.

11. The carbon supplement method according to claim 7, wherein the microalgae are *spirulina, scenedesmus, haematococcus pluvialis, Dunaliella sauna, chlorella* or *chlamydomonas*.

* * * * *